(12) United States Patent
Lin et al.

(10) Patent No.: US 11,759,471 B2
(45) Date of Patent: Sep. 19, 2023

(54) MODIFIED RELEASE PHARMACEUTICAL COMPOSITION AND METHOD FOR THE TREATMENT OF MENTAL DISORDERS

(71) Applicant: MEDICAL AND PHARMACEUTICAL INDUSTRY TECHNOLOGY AND DEVELOPMENT CENTER, New Taipei (TW)

(72) Inventors: Shih-Ku Lin, New Taipei (TW); Chih-Chiang Yang, New Taipei (TW); Tse-Ching Lin, New Taipei (TW); Lai-Cheng Chin, New Taipei (TW); Pei Hsuan Ho, New Taipei (TW)

(73) Assignee: MEDICAL AND PHARMACEUTICAL INDUSTRY TECHNOLOGY AND DEVELOPMENT CENTER, New Taipei (TW)

( * ) Notice: Subject to any disclaimer, the term of this patent is extended or adjusted under 35 U.S.C. 154(b) by 57 days.

(21) Appl. No.: 16/845,695

(22) Filed: Apr. 10, 2020

(65) Prior Publication Data
US 2020/0323875 A1    Oct. 15, 2020

Related U.S. Application Data

(60) Provisional application No. 62/833,240, filed on Apr. 12, 2019.

(51) Int. Cl.
| | |
|---|---|
| A61K 31/554 | (2006.01) |
| A61K 31/5513 | (2006.01) |
| A61K 31/551 | (2006.01) |
| A61K 9/28 | (2006.01) |
| A61K 31/519 | (2006.01) |
| A61K 31/496 | (2006.01) |
| A61K 31/38 | (2006.01) |

(52) U.S. Cl.
CPC ............. *A61K 31/554* (2013.01); *A61K 9/28* (2013.01); *A61K 31/38* (2013.01); *A61K 31/496* (2013.01); *A61K 31/519* (2013.01); *A61K 31/551* (2013.01); *A61K 31/5513* (2013.01)

(58) Field of Classification Search
None
See application file for complete search history.

(56) References Cited

U.S. PATENT DOCUMENTS 5,376,384 A * 12/1994 Eichel ................. A61P 9/08
                                                      424/480
6,958,161 B2 * 10/2005 Hayes ................. A61K 9/2081
                                                      424/463
8,858,996 B2    10/2014 Plachetka

FOREIGN PATENT DOCUMENTS

WO    WO-2005065639 A2 *  7/2005 ........... A61K 31/155
WO    WO2011085188           7/2011

OTHER PUBLICATIONS

Daller (Antipsychotic Medications, dated Jun. 21, 2017). (Year: 2017).*
Leucht et al. (Dose Equivalents for second-generation antipsychotics: The minimum effective dose method, Schizophrenia Bulletin, vol. 40, Issue 2, Mar. 2014, pp. 314-326). (Year: 2014).*
Meola et al. (The effect of drug ionization of lipid based formulations for the oral deliver of anti-psychotics, ADMET DMPK, 2020; 8(4):437-451), (Year: 2020).*

* cited by examiner

*Primary Examiner* — Melissa S Mercier
(74) *Attorney, Agent, or Firm* — Muncy, Geissler, Olds & Lowe, P.C.

(57) ABSTRACT

The present invention is concerned with a modified release pharmaceutical composition comprising an effective amount of at least one antipsychotic agent so that the antipsychotic agent(s) are released in such a manner to better accord with physiological and chronotherapeutic requirements of patients.

20 Claims, 2 Drawing Sheets

MODIFIED RELEASE PHARMACEUTICAL COMPOSITION AND METHOD FOR THE TREATMENT OF MENTAL DISORDERS

CROSS-REFERENCE TO RELATED APPLICATIONS

This non-provisional application claims priority under 35 U.S.C. § 119(a) on Patent Application No(s). 62/833,240 filed in American United States Apr. 12, 2019, the entire contents of which are hereby incorporated by reference.

FIELD OF INVENTION

The present invention relates to a modified release pharmaceutical composition for the treatment of mental disorders. More specifically, the present invention relates to a modified release pharmaceutical composition which comprises at least an antipsychotic agent or a combination thereof and optionally a carrier for modified release providing an optimized duration of effect when administered in accordance with chronotherapy to benefit patient compliance with medication.

BACKGROUND OF INVENTION

The acute phase in schizophrenia treatment features multiple dosing on a daily basis, whereas the priority during maintenance phase of schizophrenia treatment involves one medicament administration before bedtime. In general, dosage forms or formulation design controls should be taken into consideration so as to minimize the occurrence or impact level about how variable factors influence efficacy and safety of the pharmaceutical product. However, a number of established pharmaceutical formulations in the art are subject to inefficiencies leading to usability, manufacturing, or associated technical issues. For example, although established formulations leveraging on osmotic pump to delivery paliperidone is designed for uptake in the morning and could provide some beneficial usability, papliperidone, due to its long plasma half-life, does not necessarily require its currently available extended release formulation in clinical practice. An illustrative example is Invega Sustenna (paliperidone palmitate extended-release injectable suspension). Such arts feature osmotic-controlled release oral delivery systems (OROS), but its comparative advantage over the free-form of paliperidone may be marginal in view of clinical efficacy. This may be because paliperidone's half-life in patients' blood is approximately 20-28 hours (as measured by blood concentration), and such pharmacokinetic feature is already sufficient to provide reasonable pharmacological effects.

As more understandings of chronotherapeutics are built upon, delivery systems delivering only extended release is no longer sufficient for the need of achieving desirable plasma levels of drugs to synchronize with a patient's physiological biorhythms and drug reactions. There exists a need for a drug delivery system capable of adaptive and versatile delivery patterns with the potential of any preferable release timing and duration, to improve patients' compliance while not offsetting original therapeutic effects.

It is considered preferable by artisans skilled in the relevant art to provide a modified release delivery system configurable to deliver antipsychotic agent(s) so that antipsychotic agent(s)' plasma concentration profile and release rates can be better aligned with physiological and chronotherapeutic requirements.

SUMMARY OF THE INVENTION

In recognition of above, involving the need to improve sleep patterns and QOL (quality of life) of patients at present and compliance for taking drugs, the current disclosure provides a modified release pharmaceutical composition directed to dose optimization or release modification to better reflect chronotherapeutic requirements, or the half-life characteristics of drugs for patients in need thereof. The modified release pharmaceutical composition preferably comprises formulations to maintain or enhance bioavailability from a two active agents treatment approach, aiming to provide improved treatment outcome.

A first aspect of the present invention deals with a modified release pharmaceutical composition incorporating multiple active agents, in particular antipsychotic agents, for patients' benefit in taking drug once before bedtime every 24 hours. This provides an advantage of dosing compliance for the current standard of care for patients with schizophrenia, particularly for those characterized with dosing paliperidone in the morning, and quetiapine in the evening.

Another aspect of the modified release pharmaceutical composition of the present invention is the immediate release of at least an antipsychotic agent having a hypersomnia-inducing characteristic provided for ease of falling into sleep for patients, such antipsychotic agent includes but is not limited to quetiapine. Herein is provided a modified release pharmaceutical composition for drug combination featuring phasic drug release. The composition may comprise quetiapine of 25 mg for immediate release (IR) and paliperidone of 3 mg for delayed-release (DR). Such composition is more useful for providing a one-time consumption at night, allowing for improved sleep quality, and reducing the need to take additional sleeping pills, such as benzodiazepine.

Another advantage of the modified release pharmaceutical composition of the present invention is the immediate release of at least an antipsychotic agent having a hypersomnia-inducing characteristic, followed by delayed release of a different identity of an antipsychotic agent.

The above-mentioned modified release pharmaceutical composition aims at a modified release of antipsychotic agents in a predetermined pattern to reduce and delay the peak plasma concentration without affecting the extent of drug availability.

A primary objective of the present invention is to provide a modified release pharmaceutical composition for the treatment of mental disorders in a patient in need thereof, comprising:

1) an immediate release formulation containing a first antipsychotic agent in an amount effective to induce sedation in the patient; and
2) a delayed release formulation containing a second antipsychotic agent in an amount effective to treat mental disorders,
   wherein after exposure of the modified release composition to an aqueous solution, the release of the first antipsychotic agent coordinates with the second antipsychotic agent, so as to permit the time to reach the maximum blood concentration or release rate produced by the modified release composition to accord with the chronotherapeutic regime of the patient.

In an embodiment of the present invention, the delayed release formulation comprises a core comprising the first antipsychotic agent; a barrier layer covering the core; and a release controlling layer, wherein the release controlling layer comprises a pH dependent and dissolvable polymeric material having a critical pH value of about 5.5 or more, wherein a weight percentage of the release controlling layer present in the delayed release formulation containing the second antipsychotic agent is at least about 60 wt %.

In an embodiment of the present invention, the modified release composition provides administration once before bedtime every 24 hours.

In an embodiment of the present invention, the modified release composition simultaneously releases the first antipsychotic agent and the second antipsychotic agent after exposure of the modified release pharmaceutical composition to the aqueous solution.

In an embodiment of the present invention, the modified release composition rapidly releases for about 2, 3, 4, 5, 6, 7 or 8 hours, followed by releasing the second antipsychotic agent after exposure of the modified release pharmaceutical composition to the aqueous solution.

In an embodiment of the present invention, the release amount of the first antipsychotic agent is about within 90% after exposure of the modified release pharmaceutical composition to the aqueous solution to within 20 minutes.

In an embodiment of the present invention, the release amount of the second antipsychotic agent is smaller than or equal to 0%, or smaller than or equal to 10% after exposure of the modified release pharmaceutical composition to the aqueous solution.

In an embodiment of the present invention, the pH value of the aqueous solution changes from 1.5~4 to 5.6~8.0. In another embodiment of the present invention, the temperature of the aqueous solution is 35° C. to 42° C.

In an embodiment of the present invention, the modified release pharmaceutical composition releases the second antipsychotic agent from about 2, 3, 4, 5, 6, 7, or 8 hours after the time when the maximum serum plasma concentration ($T_{max}$) of the first antipsychotic agent is reached.

In an embodiment of the present invention, the mental disorder comprises schizophrenia or bipolar disorder.

In an embodiment of the present invention, the first antipsychotic agent comprises multi-acting receptor targeted antipsychotics (MARTAs) selected from the group consisting of quetiapine, clozapine, olanzapine, and zotepine.

In an embodiment of the present invention, the second antipsychotic agent comprises serotonin dopamine antagonist (SDAs), dopamine receptor partial agonist, serotonin 1A receptor agonist, or 2A receptor antagonist.

In an embodiment of the present invention, the serotonin dopamine antagonist (SDAs) is selected from the group consisting of paliperidone, risperidone, ziprasidone, and lurasidone.

In an embodiment of the present invention, the dopamine receptor partial agonist, serotonin 1A receptor agonist, or 2A receptor antagonist comprises aripiprazole.

In an embodiment of the present invention, the immediate release formulation is formulated into a granule.

In another embodiment of the present invention, the delayed release formulation is formulated into a tablet or a controlled release film coated tablet.

In an embodiment of the present invention, the first antipsychotic agent is quetiapine, and the second antipsychotic agent is paliperidone.

In an embodiment of the present invention, the first antipsychotic agent in the amount effective to induce sedation in the patient is 2.5 mg-300 mg, and the second antipsychotic agent in the amount effective to treat mental disorders is 1 mg-6 mg.

In an embodiment of the present invention, the modified release pharmaceutical composition further comprises a carrier, the immediate release formulation and the delayed release formulation are filled into the carrier.

In an embodiment of the present invention, the carrier comprises a capsule, a tablet, a packet, or a granule.

In an embodiment of the present invention, the tablet comprises a standard tablet, a sugar coated tablet, a film coated tablet, a matrix tablet, a functionally coated tablet, a mini tablet, a multiple compressed tablet, or a controlled release film coated tablet.

In an embodiment of the present invention, a dosage form of the immediate release formulation is granule.

In an embodiment of the present invention, a dosage form of the delayed release formulation is tablet or controlled release film coated tablet.

In an embodiment of the present invention, a dosage form of the delayed release formulation encapsulated or embeds a dosage form of the immediate release formulation.

Another primary objective of the present invention is to provide a method of treating schizophrenia or bipolar disorder, which comprises administering a modified release pharmaceutical composition described therein to a patient.

In an embodiment of present invention, the method comprises administering the modified release pharmaceutical composition to the patient once before bedtime every 24 hours.

BRIEF DESCRIPTION OF THE DRAWINGS

The following drawings form part of the present specification and are included to further demonstrate certain aspects of the present invention. The invention may be better understood by reference to one or more of the drawings in combination with the detailed description of specific embodiments presented herein.

DETAILED DESCRIPTION OF THE INVENTION

Figure 1:
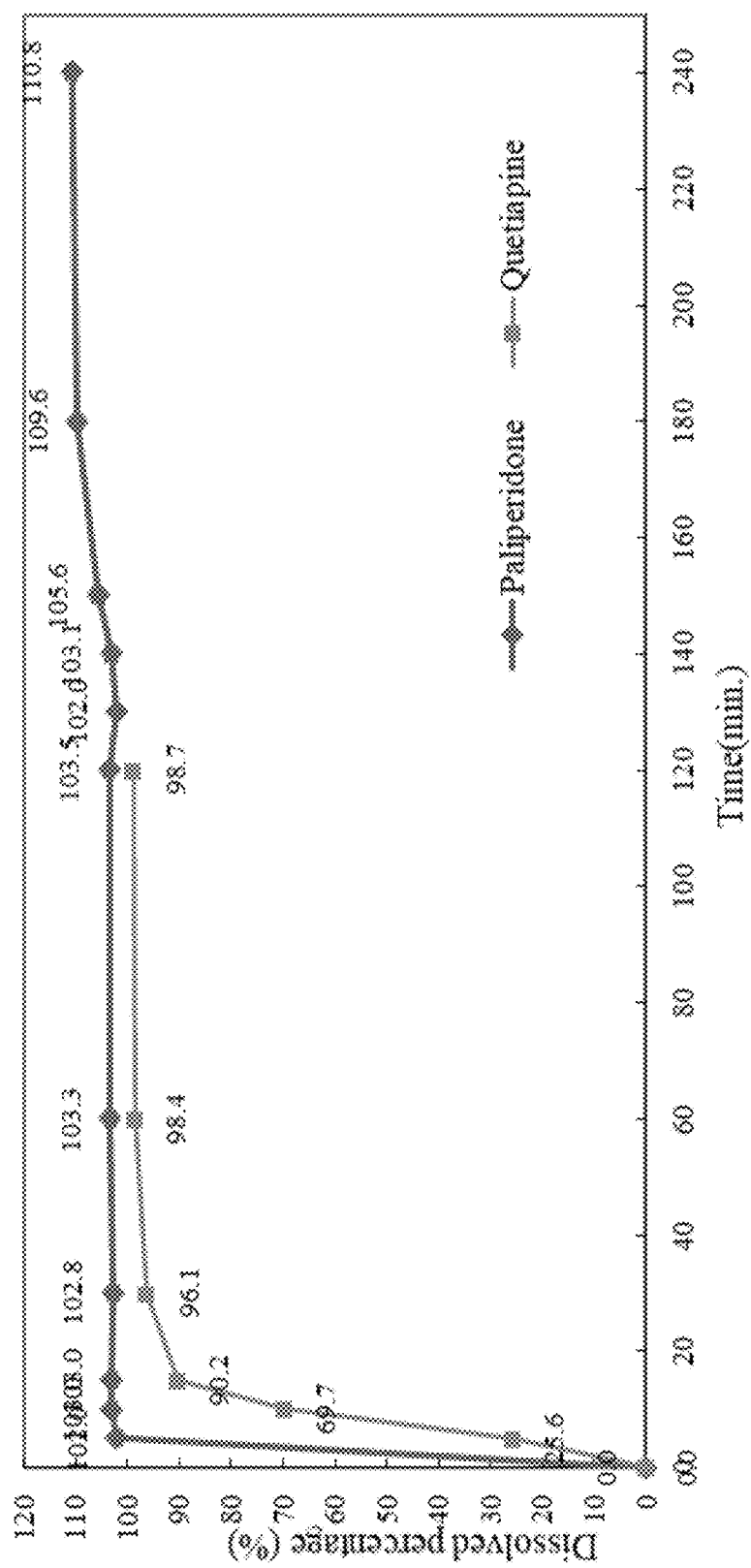
FIG. 1—In Vitro Dissolution profile of immediate release of quetiapine and immediate release of paliperidone.

In recognition of above, the current disclosure provides a modified release pharmaceutical composition, the pharmaceutical composition preferably comprises formulations to maintain or enhance bioavailability effectuated from a two active agents treatment approach, providing improved sleep pattern and QOL as well as medication compliance.

As used herein "immediate release" means that release of the antipsychotic agent is not significantly delayed by means of a carrier or physiological process. The excipients used to achieve immediate release typically dissolve or disperse rapidly in gastric fluid.

"Delayed release" means that there is a period of time after the dosage form contacts gastric fluid during which the antipsychotic agent either is not released or is released at a rate that is not therapeutically effective for the purpose that the drug has been administered to the patient.

"Immediate release" may be coupled with delayed release so that release of the antipsychotic agent according to that profile begins after a delay period in which the antipsychotic agent either is not released or is released at a rate that is not therapeutically effective for the purpose that the drug has been administered to the patient.

"Modified release" is used inclusively to mean immediate release; delayed release; immediate release, followed by delayed release; and any release other than immediate release.

"Chronopharmacokinetics" refers to variations in pharmacokinetics of the patient during the 24 hours timespan.

As described above, with regard to the range of plasma concentrations, there is no particular limitation provided that, the antipsychotic agent, which functions as the active substance, maintains plasma level which is pharmacologically effective for therapy or prevention of the disorder when a pharmaceutical composition containing at least an antipsychotic agent or a combination thereof and a carrier for the modified release pharmaceutical preparation is administered.

The present invention provides a modified release pharmaceutical composition for the treatment of mental disorders. More specifically, the release by the modified release pharmaceutical composition permits the time to reach the maximum blood concentration or release rate produced thereby to accord with the chronotherapeutic regime of the patient. In an embodiment, the pharmaceutical composition is suitable for administration once before bedtime every 24 hours to the patient.

The mental disorders described herein comprise schizophrenia or bipolar disorder.

A primary objective of the present invention is to provide a modified release pharmaceutical composition for the treatment of mental disorders in a patient in need thereof, comprising:
1) an immediate release formulation containing a first antipsychotic agent in an amount effective to induce sedation in the patient; and
2) a delayed release formulation containing a second antipsychotic agent in an amount effective to treat mental disorders,
   wherein after exposure of the modified release composition to an aqueous solution, the release of the first antipsychotic agent coordinates with the second antipsychotic agent, so as to permit the time to reach the maximum blood concentration or release rate produced by the modified release composition to accord with the chronotherapeutic regime of the patient.

The present invention relates to a pharmaceutical composition comprising a first antipsychotic agent and a second antipsychotic agent, wherein the first antipsychotic agent and the second antipsychotic agent are simultaneously or sequentially administered to a patient.

In an aspect of the present invention, the first antipsychotic agent in the modified release pharmaceutical composition present in an amount effective to induce sedation in the patient ranges in weight between 2.5 mg-300 mg. The first antipsychotic agent comprises multi-acting receptor targeted antipsychotics (MARTAs) selected from the group consisting of quetiapine, clozapine, olanzapine, and zotepine. In an embodiment, the first antipsychotic agent is quetiapine, whose weight ranges between 25 mg-300 mg, preferably 25 mg. The first antipsychotic agent comprises, but not exclusively, a sedative antipsychotic agent.

In another aspect of the present invention, the second antipsychotic agent in the modified release pharmaceutical composition present in an amount effective to treat mental disorders in the patient ranges in weight between 2.5 mg-300 mg. The second antipsychotic agent comprises serotonin dopamine antagonist (SDAs), dopamine receptor partial agonist, serotonin 1A receptor agaonist, or 2A receptor antagonist. In an embodiment, the second antipsychotic agent is paliperidone, whose weight ranges between 1 mg-6 mg, preferably 3 mg. The dopamine receptor partial agaonist, serotonin 1A receptor agonist, or 2A receptor antagonist comprises, but not exclusively, aripiprazole.

Yet another aspect of the present invention provides a manufacturing process. In an embodiment, the process comprises the following steps: (1) preparing granules of a first antipsychotic agent in an amount effective to induce sedation in a patient, (ii) tableting the second antipsychotic agent in an amount effective to treat mental disorders, (iii) preparing a release controlling layer solution, and coating the tablets prepared from Step (ii) with the release controlling layer solution, and (iv) filling the granules and the controlled release coated tablets into the capsule. The process involved in each production step may be reasonably adjusted, while maintaining the same basic production steps, to compensate for different equipment characteristics, and/or on the basis of experience.

In an embodiment of the present invention, the administration of the modified release pharmaceutical composition for treating mental disorders may be realized by way of any of the following drug release modes, including but not limited to (A) simultaneous immediate release multiple-units formulations, (B) stepwise two-phase-release multiple-units formulations.

(A) Simultaneous Immediate Release Multiple-Units Formulations

A formulation used here allows for immediate release of multiplicity of individual antipsychotic agents contained in the formulations in such a form that the individual antipsychotic agents will be made available to the patient upon disintegration of the formulation.

In an embodiment, a first antipsychotic agent is formulated in an immediate release formulation, and the second antipsychotic agent is formulated in an immediate release formulation.

In some embodiments, the immediate release formulation of the first antipsychotic agent releases the first antipsychotic agent within 1 hour after administration of the pharmaceutical composition to the patient. In some embodiments, the immediate release formulation of the first antipsychotic agent releases the first antipsychotic agent within 10, 20, 30, 40, 50 minutes after administration of the pharmaceutical composition to the patient. In some embodiments, the immediate release formulation of the second antipsychotic agent releases the second antipsychotic agent within 1 hour after administration of the pharmaceutical composition to the patient. In some embodiments, the immediate release formulation of the second antipsychotic agent releases the second antipsychotic agent within 10, 20, 30, 40, 50 minutes after administration of the pharmaceutical composition to the patient.

(B) Stepwise Two-Phase-Release Multiple-Units Formulations

Stepwise, two-phase release multiple-units formulations allow for a first antipsychotic agent to be administered immediately following administration of the pharmaceutical composition to a patient, before a delayed release of a second antipsychotic agent to the human patients thereof occurs. "Stepwise" herein refers to a series of distinct pharmacological drug delivery periods. "Two-phase" herein refers to two periods of distinct drug delivery mechanism (e.g. immediate release and delay release).

In an embodiment, a first antipsychotic agent is formulated into an immediate release formulation, and a second antipsychotic agent is formulated in a delayed release formulation.

In an embodiment, a first antipsychotic agent is formulated in an immediate release formulation, and a second antipsychotic agent is formulated in a delayed release formulation.

The immediate release formulation and delayed release formulation of the modified release pharmaceutical composition are not particularly limited herein, which are pharmaceutically acceptable and may operate individually or in combination to realize any of a wide variety of prescribed immediate and controlled release profiles.

In an aspect of a prescribed immediate and delayed release profiles envisioned by the present invention, the time to reach maximum plasma concentration ($T_{max}$) of the second antipsychotic agent is equal to or greater than the elimination half-life ($t_{1/2}$) of the first antipsychotic agent.

In another aspect of a prescribed immediate and delayed release profiles envisioned by the present invention, the first antipsychotic agent is rapidly released while the second antipsychotic agent is released until after a period of time. In some embodiments, the first antipsychotic agent is rapidly released while the second antipsychotic agent is released until after a period of time from about 2, 3, 4, 5, 6, 7, or 8 hours after exposure of the pharmaceutical composition to an aqueous solution. In a preferred embodiment, the first antipsychotic agent is rapidly released while the second antipsychotic agent is released until after a period of time from about 2, 3, 4, 5, 6, 7, or 8 hours after exposure of the pharmaceutical composition to an aqueous solution having a pH of between 1 and 6. In an embodiment, the first antipsychotic agent is rapidly released while the second antipsychotic agent is released until after a period of time from about 2, 3, 4, 5, 6, 7, or 8 hours after exposure of the pharmaceutical composition to an aqueous solution having a pH value changing from 1.5~4.5 to 5.6~8.0 a temperature of between 35° C. and 42° C. In the foregoing embodiment, the first antipsychotic agent is released within 1 hour or within 10, 20, 30, 40, 50 minutes after administration of the pharmaceutical composition to the patient.

In still another aspect of a prescribed immediate and delayed release profiles envisioned by the present invention, the second antipsychotic agent provides the maximum serum plasma concentration at a time ($T_{max}$) equal to or greater than the time when the maximum serum plasma concentration ($T_{max}$) of the first antipsychotic agent is reached. In yet still another aspect of the present invention, the second antipsychotic agent is released after a period of time from about 2, 3, 4, 5, 6, 7, or 8 hours after the time when the maximum serum plasma concentration ($T_{max}$) of the first antipsychotic agent is reached.

In a further aspect of a prescribed immediate and delayed release profiles envisioned by the present invention, the immediate release formulation of the first antipsychotic agent releases the first antipsychotic agent within 1 hour after administration of the pharmaceutical composition to the patient. In some embodiments, the immediate release formulation of the first antipsychotic agent releases the first antipsychotic agent within 10, 20, 30, 40, 50 minutes after administration of the pharmaceutical composition to the patient.

The foregoing delayed release formulation may be realized by way of a drug release mode, (a) immediate release single-unit formulation, and (b) delayed release single-unit formulation.

(a) Immediate Release Single-Unit Formulation: An immediate release single-unit formulation provides for immediate release of an individual antipsychotic agent contained in the formulation upon disintegration of the formulation.

(b) Delayed Release Single-Unit Formulation: A delayed release single-unit formulation provides for delayed release of an individual antipsychotic agent contained in the formulation in a manner that can be exemplified as the following.

In an aspect of the present invention, the antipsychotic agent is administered 2 hours before said antipsychotic agent's elimination half-life. In some embodiments, the antipsychotic agent is administered at least 2 hours before bed. In some embodiments, the antipsychotic agent is 100% released from the formulation within 2 hours of administration.

In some embodiments, the antipsychotic agent is 100% released from the formulation within 4 hours of administration In some embodiments, the antipsychotic agent is 100% released from the formulation within 5 hours of administration.

In some embodiments, the antipsychotic agent is 100% released from the formulation within 6 hours of administration In an aspect of the present invention, a carrier used for the delayed-released single-unit formulation comprises a multi-layered structure. In some embodiments, the carrier comprises a drug-containing core and a release controlling layer(s). In some embodiments, the carrier comprises a release controlling layer(s). In some embodiments, the release controlling layer(s) is formulated in a delayed-release coating or a controlled-release coating.

The foregoing coatings may comprise methacrylic acid, ethyl cellulose, hypromellose (HPMC), polyethylene glycol (PEG).

In some embodiments, the foregoing coatings of methacrylic acid was tested and the results showed that it would not dissolve in a solvent of pH1.2. Further use carried out with different encapsulation efficiency of experiments, and the samples with different encapsulation efficiency were test pH1.2 solvent dissolve. At the same time, it can be known that the results of the dissolution rate of paliperidone within 2 hours is not more than 10%. The present invention can be achieved effect of delayed release of paliperidone.

For the development of the technical type of the invention, the experimental design takes 2-4 hours as the design objective. In actual development, the invention artificial determines that the test medium is changed second hours after taking so that the release controlling layer of delayed release of (B) can play a releasing role. Taking the acrylic resin (L30D55) in the release control layer of delayed release of (B) as an example, paliperidone can only be released when pH value is above 5.5. The release control layer of the delayed release of (B) must be coated to isolate the gastric acid reaction and to achieve second hour release.

In addition, the drug stays in the stomach for about 1~3 hr after administration, and the pH value is 1.5~4.5 (actual value variable with subject in fasted state or non-fasted state). During this stage, paliperidone will not be released, and the pH value will gradually rise to about 5.6~8.0 after the drug is transported out from the stomach to the small intestine (duodenum, jejunum and ileum). When the pH value of the drug is greater than 5.5, the modified release pharmaceutical composition begins to dissolve and release. The purpose of the enteric-coated tablets (capsules) is to allow the drug to remain in the stomach without being released until it is released in the intestine, so as to achieve a delayed release outcome.

In some embodiments, the carrier comprises at least two concentric layers.

In another aspect of the present invention, the carrier used for the delayedrelease single-unit formulations is a delayed release excipient embedded or encapsulated with the antipsychotic agents. In some embodiments, the carrier is selected from the group consisting of polar or non-polar lipids, non-ionic surfactant-based vesicles, but not limited to the list hereof.

Dosage Forms

The units prepared according to an aspect of the present invention may be incorporated in a carrier, including but not limited to conventional pharmaceutical dosage forms such as a standard tablet, a granule, a pellet, a capsule, an orally administered form.

In some embodiments, tablets comprise a standard tablet, a sugar-coated tablet, a film coated tablet, a matrix tablet, a functionally coated tablet, a mini tablet, a multiple compressed tablet, an controlled release film coated tablet.

In some embodiments, the immediate release formulation is formulated into a standard tablet, a granule, a film coated tablet, a mini tablet.

In some embodiments, the delayed release formulation is formulated into a tablet or a controlled release coated tablet.

The units prepared according to another aspect of the present invention may further comprise a carrier, for example an immediate release formulation of a first antipsychotic agent and a delayed release formulation of a second antipsychotic agent, are filled, dispersed, suspended, or encapsulated inside the carrier, though not limited to the list hereof.

In some embodiments, the carrier is formulated into a dosage form comprising a capsule, a tablet, a packet, a granule.

In some embodiments, the tablet comprises a standard tablet, a sugar-coated tablet, a film coated tablet, a matrix tablet, a functionally coated tablet, a mini tablet, a multiple compressed tablet, or an controlled release film coated tablet.

Active Ingredient Makeup

The antipsychotic agent makeup of each modified release pharmaceutical composition comprises at least an antipsychotic agent or a combination thereof.

The antipsychotic agent which is subject to modified release may be (A) multi-acting receptor targeted antipsychotics (MARTA), (B) serotonin dopamine antagonist (SDA), or (C) dopamine receptor partial agonist, serotonin 1A receptor agonist, and 2A receptor antagonist.

The antipsychotic agents fitting criterion of (A) comprises quetiapine, clozapine, olanzapine, zotepine, though not limited to the list hereof. The antipsychotic agents fitting criterion of (B) comprises paliperidone, risperidone, ziprasidone, lurasidone, though not limited to the list hereof.

In some embodiments of a modified release pharmaceutical composition containing an antipsychotic agent, the antipsychotic agent therein is the antipsychotic agent fitting criterion of (B).

In some embodiments, a modified release pharmaceutical composition comprises an antipsychotic agent, the antipsychotic agent therein is formulated in an immediate release (IR) formulation, delayed release (DR) formulation, or controlled release (CR) formulation.

Combination herein comprises a first antipsychotic agent and a second antipsychotic agent. In some embodiments, the first antipsychotic agent or the second antipsychotic agent comprises typical or atypical antipsychotic agent, preferably atypical antipsychotic agent.

In some embodiments, the foregoing combination comprises a first antipsychotic agent fitting criterion of (A) and a second antipsychotic agent fitting criterion of (C), or (A) and (B) respectively of the first and the second antipsychotic agent, or (B) and (C) respectively of the first and the second antipsychotic agent.

In some embodiments, the foregoing combination comprises a first antipsychotic agent formulated in an immediate release formulation, and a second antipsychotic agent formulated in an immediate release formulation. In further embodiments, the first and the second antipsychotic agents are formulated in such a manner to immediately release the first antipsychotic agent.

In some embodiments, the foregoing combination comprises a first antipsychotic agent formulated in an immediate release formulation, and a second antipsychotic agent formulated in a delayed release formulation. In further embodiments, the first and the second antipsychotic agents are formulated in stepwise, two-phase release formulation. In yet further embodiments, the first and the second antipsychotic agents are formulated in such a manner to delay release the second antipsychotic agent.

In some embodiments, the first antipsychotic agent contained in the foregoing combination comprises quetiapine, and the second antipsychotic agent contained therein comprises paliperidone. In some other embodiments, the first and the second antipsychotic agent contained in the foregoing combination comprises quetiapine formulated in an immediate release formulation, and paliperidone formulated in an immediate release formulation. In yet other embodiments, the foregoing combination comprises quetiapine formulated in an immediate release formulation, and paliperidone formulated in a delayed release formulation.

Method of Use for Treating Schizophrenia

The present invention also provides for a method of use for treating schizophrenia or bipolar disorder, which comprises administering the foregoing modified release pharmaceutical composition to a patient in need thereof.

An aspect of the present invention comprises using the modified-release pharmaceutical composition to simultaneously or sequentially administer a first antipsychotic agent and a second antipsychotic agent. In some embodiments, the first antipsychotic agent is administered in an immediate release composition. In some embodiments, the second antipsychotic agent is administered in an immediate release composition or a delayed release composition.

Another aspect of the present invention comprises using the modified release pharmaceutical composition to administer an antipsychotic agent. In some embodiments, the antipsychotic agent is administered in a delayed release composition.

EXAMPLES

The present invention will be further described by way of the following examples including but not limited to analytical methods, experimental methods, manufacture processes, formulations. The following examples are offered for illustrative purposes, and are not intended to limit the invention in any manner. Those of skill in the art will readily recognize a variety of noncritical parameters which can be changed or modified to yield essentially the same results.

Manufacturing Process

Example 1

Delayed-Release Single-Unit Formulation

Paliperidone Formulation (QPC-P-009)

Process 1: Tableting

| Ingredients | Unit Content ([mg]) | Weight Percentage [%] | Function |
|---|---|---|---|
| Paliperidone | 6.00 | 6.00% | API |
| Lactose Monohydrate (Flow Lac 100) | 69.00 | 69.00% | Filler |
| Starch 1500 | 23.30 | 23.30% | Filler |
| L-HPC (LH-21) | 1.00 | 1.00% | Disintegrant |
| Magnesium Stearate | 0.70 | 0.70% | Lubricant |
| Total | 100.00 | 100.00% | — |

Process 2: Coating (Barrier Layer)
Composition of Barrier Layer

| | | Weight Percentage [%] |
|---|---|---|
| Polymer | Opadry Clear 03k19229(HPMC) | 7.41% |
| Solvent | Water | 92.59% |
| Total | — | 100.00% |

Process 3: Coating (Release Controlling Layer)
Composition of Release Controlling Layer

| | | Weight Percentage [%] |
|---|---|---|
| Polymer | Eudragit L30D55 | 60.75% |
| Plasticizer | Triethyl Citrate (TEC) | 0.98% |
| Anti-Tacking | T20 | 1.82% |
| Solvent | Water | 36.45% |
| Total | — | 100.00% |

Example 2

Simultaneous-Immediate-Release Multiple-Units Formulation

To an amount of 3 mg of paliperidone was added an amount of 25 mg of quetiapine (Seroquel) was subjected to a dissolution analysis.

Example 3

Stepwise and Two-Phase Release Multiple-Units Formulation

In general, quetiapine and paliperidone formulation (e.g. QPC-P-009) were co-filled into a capsule to prepare a finalized product (e.g. QPC-QP-003), the capsule was subjected to an analysis.

1. Quetiapine Formulation (e.g. QPC-Q-012)
Composition of Quetiapine Formulation (QPC-Q-012)

| Ingredients | Unit Content [mg] | Weight Percentage [%] | Function |
|---|---|---|---|
| Quetiapine Fumarate | 28.79 | 28.8% | API |
| Microcrystalline Cellulose (MCC 101) | 28.71 | 28.7% | Filler |
| Lactose Monohydrate (Lactose 200) | 33.00 | 33.0% | Filler |
| Povidone (PVP K30) | 5.00 | 5.0% | Binder |
| Sodium Starch Glycolate | 3.50 | 3.5% | Disintegrant |
| Magnesium Stearate | 1.00 | 1.0% | Lubricant |
| Water | — | — | Solvent |
| Total | 100.00 | 100.0% | — |

2. Paliperidone Formulation (QPC-P-009)
Process 1: Tableting

| Ingredients | Unit Content [mg] | Weight Percentage [%] | Function |
|---|---|---|---|
| Paliperidone | 6.00 | 6.00% | API |
| Lactose Monohydrate (Flow Lac 100) | 69.00 | 69.00% | Filler |
| Starch 1500 | 23.30 | 23.30% | Filler |
| L-HPC (LH-21) | 1.00 | 1.00% | Disintegrant |
| Magnesium Stearate | 0.70 | 0.70% | Lubricant |
| Total | 100.00 | 100.00% | — |

Process 2: Coating (Barrier Layer)
Composition of Barrier Layer

| | | Weight Percentage [%] |
|---|---|---|
| Polymer | Opadry Clear 03k19229(HPMC) | 7.41% |
| Solvent | Water | 92.59% |
| Total | — | 100.00% |

Process 3: Coating (Release Controlling Layer)
Composition of Release Controlling Layer

| | | Weight Percentage [%] |
|---|---|---|
| Polymer | Eudragit L30D55 | 60.75% |
| Plasticizer | Triethyl Citrate (TEC) | 0.98% |
| Anti-Tacking | T20 | 1.82% |
| Solvent | Water | 36.45% |
| Total | — | 100.00% |

3. Filling Quetiapine and Paliperidone Into a Capsule (QPC-QP-003)

Granulated powder of quetiapine formulation (e.g. QPC-Q-012) and control-releasing-layer-coated tablet (QPC-P-009) were combined (QPC-QP-003) and filled into a Size 1 White Gelatin Capsule.

Dissolution Test

In vitro dissolution test was conducted in a USP Apparatus 2 (paddle) at 37±0.5° C., 50 rpm, in a solution having 750 mL of 0.1 N HCl and 1000 mL of pH 6.8 buffer FIG. 1 discloses the dissolution release amount for 25 mg quetiapine in tablet of reference listed drug, 3 mg paliperidone in raw form.

In FIG. 1, within 20 minutes after quetiapine in tablet of reference listed drug was disposed in the dissolution solution, its highest dissolution amount was merely about 90%. Less than 10 minutes after paliperidone in raw form was disposed in the prescribed environment, its dissolution amount already passed 100%, and continued to maintain a dissolution amount above 100%. If 120 minutes passed after paliperidone in raw form began to dissolve, the pH value of the aqueous solution that the paliperidone in raw form was disposed in increased from 1.2 to 6.8, the dissolution amount would slightly decrease, but continued to maintain above 100%.

Figure 2:
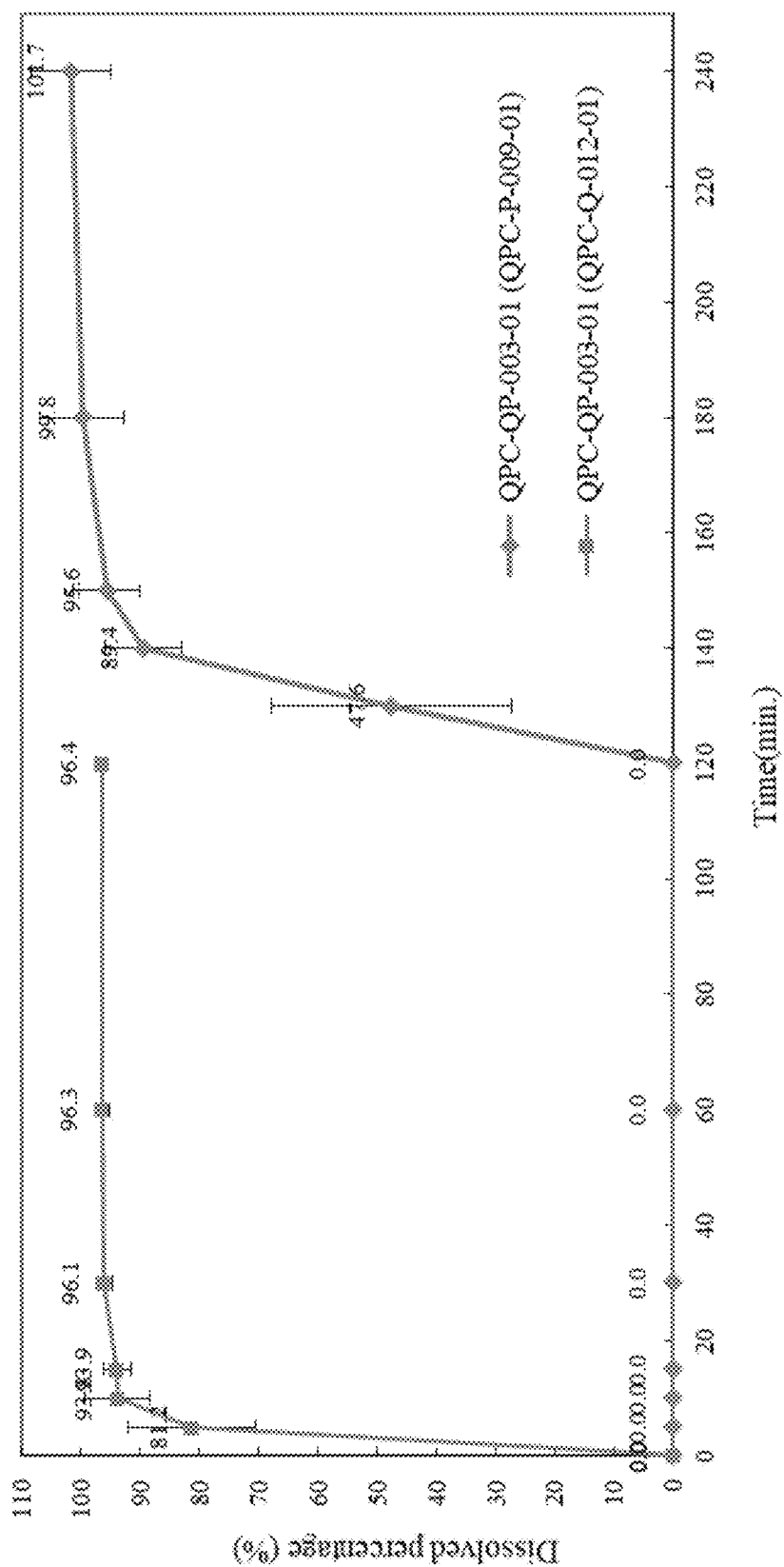
FIG. 2—In Vitro Dissolution profile of immediate release of quetiapine, followed by delayed release of paliperidone.

It can be observed in FIG. 2 that the modified release pharmaceutical composition began releasing quetiapine after it was exposed to the aqueous solution, and then when it had cumulatively release to 20 minutes, the release amount of quetiapine passed above 90%. When the modified release pharmaceutical composition began releasing quetiapine, it did not release paliperidone. After the modified release pharmaceutical composition began releasing quetiapine to 2 hours (i.e. 120 minutes), aqueous solution that the modified release pharmaceutical composition was exposed in underwent a change, permitting the modified release pharmaceutical composition to begin releasing paliperidone. During the course the modified release pharmaceutical composition began releasing quetiapine and 120 minutes thereafter, the pH value of the aqueous solution increased to about 6.8, and it was at this point the modified release pharmaceutical composition began releasing paliperidone (i.e. the dissolution amount of paliperidone being greater than 0%). Within 20 minutes since the modified release pharmaceutical composition began releasing paliperidone, the highest dissolution amount of paliperidone was about 90%.

The invention claimed is:

1. A modified release pharmaceutical composition for the treatment of mental disorders in a patient in need thereof comprising:
1) An immediate release formulation containing a first antipsychotic agent in an amount effective to induce sedation in the patient; and
2) a delayed release formulation containing a second antipsychotic agent in an amount effective to treat mental disorders, wherein the delayed release formulation comprises a core comprising the second antipsychotic agent; a barrier layer covering the core; and a release controlling layer, wherein the release controlling layer comprises a pH dependent and dissolvable polymeric material having a critical pH value of 5.5 or more, wherein a weight percentage of the release controlling layer presented in the delayed release formulation containing the second antipsychotic agent is at least 60 wt %,
wherein after exposure of the modified release pharmaceutical composition to an aqueous solution, release of the first antipsychotic agent coordinates with the second antipsychotic agent, so as to permit time to reach a maximum blood concentration or a release rate produced by the modified release pharmaceutical composition to accord with chronotherapeutic regime of the patient,
wherein a release amount of the second antipsychotic agent is equal to 0%, or smaller than or equal to 10% within 2 hours after exposure of the modified release pharmaceutical composition to the aqueous solution, and
wherein the modified release pharmaceutical composition is in a carrier.

2. The modified release pharmaceutical composition of claim 1, wherein the modified release pharmaceutical composition simultaneously releases the first antipsychotic agent and the second antipsychotic agent after exposure of the modified release pharmaceutical composition to the aqueous solution.

3. The modified release pharmaceutical composition of claim 1, wherein the modified release pharmaceutical composition rapidly releases for about 2, 3, 4, 5, 6, 7 or 8 hours, followed by releasing the second antipsychotic agent after exposure of the modified release pharmaceutical composition to the aqueous solution.

4. The modified release pharmaceutical composition of claim 1, wherein the pH value of the aqueous solution changes from 1.5-4.5 to 5.6-8.0.

5. The modified release pharmaceutical composition of claim 1, wherein the modified release pharmaceutical composition releases the second antipsychotic agent from about 2, 3, 4, 5, 6, 7, or 8 hours after the time when a maximum serum plasma concentration (Tmax) of the first antipsychotic agent is reached.

6. The modified release pharmaceutical composition of claim 1, wherein the mental disorder comprises schizophrenia or bipolar disorder.

7. The modified release pharmaceutical composition of claim 1, wherein the first antipsychotic agent comprises multi-acting receptor targeted antipsychotics (MARTAs) selected from the group consisting of quetiapine, clozapine, olanzapine, and zotepine.

8. The modified release pharmaceutical composition of claim 1, wherein the second antipsychotic agent comprises serotonin dopamine antagonist (SDAs), dopamine receptor partial agonist, serotonin 1A receptor agonist, or 2A receptor antagonist.

9. The modified release pharmaceutical composition of claim 8, wherein the serotonin dopamine antagonist (SDAs) is selected from the group consisting of paliperidone, risperidone, ziprasidone, and lurasidone.

10. The modified release pharmaceutical composition of claim 8, wherein the dopamine receptor partial agonist, serotonin 1A receptor agonist, or 2A receptor antagonist comprises aripiprazole.

11. The modified release pharmaceutical composition of claim 1, wherein the first antipsychotic agent is quetiapine, and the second antipsychotic agent is paliperidone.

12. The modified release pharmaceutical composition of claim 1, wherein the first antipsychotic agent in the amount effective to induce sedation in the patient is 2.5 mg-300 mg, and the second antipsychotic agent in the amount effective to treat mental disorders is 1 mg-6 mg.

13. The modified release pharmaceutical composition of claim 1, wherein the carrier comprises a capsule, a tablet, a packet, or a granule.

14. The modified release pharmaceutical composition of claim 13, wherein the tablet comprises a standard tablet, a sugar coated tablet, a film coated tablet, a matrix tablet, a functionally coated tablet, a mini tablet, a multiple compressed tablet, or an controlled release film coated tablet.

15. The modified release pharmaceutical composition of claim 1, wherein a dosage form of the immediate release formulation is granule.

16. The modified release pharmaceutical composition of claim 1, wherein a dosage form of the delayed release formulation is tablet or controlled release film coated tablet.

17. The modified release pharmaceutical composition of claim 1, wherein a dosage form of the delayed release formulation encapsulates or embeds a dosage form of the immediate release formulation.

18. A method of treating schizophrenia or bipolar disorder, the method comprising administering a modified release pharmaceutical composition to a patient in need thereof, wherein modified release pharmaceutical composition comprises:
1) An immediate release formulation containing a first antipsychotic agent in an amount effective to induce sedation in the patient; and
2) a delayed release formulation containing a second antipsychotic agent in an amount effective to treat mental disorders, wherein the delayed release formulation comprises a core comprising the second antipsychotic agent; a barrier layer covering the core; and a release controlling layer, wherein the release controlling layer comprises a pH dependent and dissolvable polymeric material having a critical pH value of 5.5 or more, wherein a weight percentage of the release controlling layer present in the delayed release formulation containing the second antipsychotic agent is at least 60 wt %,
wherein after exposure of the modified release pharmaceutical composition to an aqueous solution, release of the first antipsychotic agent coordinates with the second antipsychotic agent, so as to permit time to reach a maximum blood concentration or a release rate produced by the modified release pharmaceutical composition to accord with a chronotherapeutic regime of the patient,
wherein the modified release pharmaceutical composition is administered once before bedtime every 24 hours, and
wherein the modified release pharmaceutical composition is in a carrier.

19. A modified release pharmaceutical composition administered once before bedtime every 24 hours for the treatment of mental disorders in a patient in need thereof, wherein the modified release pharmaceutical composition comprising:
1) An immediate release formulation containing a first antipsychotic agent in an amount effective to induce sedation in the patient; and
2) a delayed release formulation containing a second antipsychotic agent in an amount effective to treat mental disorders, wherein the delayed release formulation comprises a core comprising the second antipsychotic agent; a barrier layer covering the core; and a release controlling layer, wherein the release controlling layer comprises a pH dependent and dissolvable polymeric material having a critical pH value of about 5.5 or more, wherein a weight percentage of the release controlling layer present in the delayed release formulation containing the second antipsychotic agent is at least about 60 wt %,
wherein after exposure of the modified release composition to an aqueous solution, the release of the first antipsychotic agent coordinates with the second antipsychotic agent, so as to permit the time to reach the maximum blood concentration or release rate produced by the modified release composition to accord with the chronotherapeutic regime of the patient,
wherein the release amount of the second antipsychotic agent is equal to 0%, or smaller than or equal to 10% within 2 hours after exposure of the modified release pharmaceutical composition to the aqueous solution, and
wherein the modified release pharmaceutical composition is in a carrier.

20. A method of administering a modified release pharmaceutical composition according to claim 1, wherein the modified release pharmaceutical composition is administered once before bedtime every 24 hours.

* * * * *